United States Patent [19]

Kauffmann et al.

[11] Patent Number: 4,742,832
[45] Date of Patent: May 10, 1988

[54] MUSCLE MEASURING APPARATUS AND METHOD

[76] Inventors: Richard Kauffmann, Geminis 4249, Guadalajara, Mexico; Lutz Kauffmann, Av. Parque Lira 79, Mexico D.F., Mexico, 11-850

[21] Appl. No.: 13,913

[22] Filed: Feb. 12, 1987

[51] Int. Cl.$^4$ .............................................. A61B 5/10
[52] U.S. Cl. ................................... 128/774; 128/782; 33/515; 73/862.45
[58] Field of Search ....................... 128/774, 781–782; 33/511–515; 73/862.38, 862.45

[56] References Cited

U.S. PATENT DOCUMENTS

| 1,619,491 | 3/1927 | Smith | 128/774 |
| 3,752,144 | 8/1973 | Weigie, Jr. | 128/774 |
| 4,492,233 | 1/1985 | Petrofsky et al. | 128/421 |
| 4,549,555 | 10/1985 | Fraser | 128/782 |
| 4,583,554 | 4/1986 | Mittelman et al. | 128/774 |

FOREIGN PATENT DOCUMENTS

| 2912981 | 10/1980 | Fed. Rep. of Germany | 128/774 |
| 0957860 | 9/1982 | U.S.S.R. | 128/774 |
| 0984460 | 1/1983 | U.S.S.R. | 128/774 |
| 1175433 | 8/1985 | U.S.S.R. | 128/774 |

Primary Examiner—William E. Kamm
Assistant Examiner—Angela D. Sykes
Attorney, Agent, or Firm—McCaleb, Lucas & Brugman

[57] ABSTRACT

Apparatus and method for measuring the strength of selected muscles of the human anatomy for the purpose of analyzing body symmetry and column disorders comprising an upright support frame, a force sensor and measuring device stationarily positioned on the frame, a first force transmitting member carrying a patient engageable apparatus operable to transmit forces along a horizontal axis to actuate the sensor and measuring device, a second force transmitting member carrying additional patient engageable apparatus operable to transmit forces along a vertical axis, a force transfer mechanism capable of converting forces transmitted along said vertical axis by the second member into horizontal forces transmitted by the first transmitting member, and apparatus for locating the patient in the same position during successive measuring sessions.

10 Claims, 2 Drawing Sheets

MUSCLE MEASURING APPARATUS AND METHOD

BACKGROUND OF THE INVENTION

This invention related generally to the field of muscular evaluation related to the human anatomy and more particularly to an improved apparatus and method for evaluating the strength of selected muscle groups for diagnostic purposes, particularly related to column disorders.

The prior art has developed numerous muscle measuring or testing devices, but to date little progress has been made toward the development of an operably dependable device for use by the medical profession in diagnosing muscle disorders. In point of fact, the recommended procedure for measuirng muscle efficiency remains in a relative primitive state of "hands on" evaluation in which the patient exerts muscular force against the examiner's resistance, or resistance against movement performed by the examiner. Thus, initial diagnosis as well as evaluation of subsequent test results depends on the examining physician's memory and impression of the patient's muscular abilities. Such subjective recall is not scientifically reliable.

Exercise devices also have been employed to evaluate dynamic muscle activity, but these measure the force exerted by one or more groups of muscles as opposed to individual or selected muscles. Further such exercise devices require the patient to actively participate under physical stress which is not always a reasonable requirement, especially if the patient is injured or otherwise physically impared.

A further important and practical consideration to solving the problem of diagnostic muscle evaluation is the capability of duplicating the testing conditions from time to time in order to arrive at comparative test results. Most prior developed devices for this purpose have failed to provide this capability with any acceptable certainty and as a result, test results have been subject to error.

SUMMARY OF THE INVENTION

In an effort to overcome the above noted and other deficiencies of the prior art, the muscle measuring apparatus and method of this invention provide a simplified means for measuring the strength of selected muscles of the human anatomy while insuring that subsequent measurements thereof may be made under duplicate testing conditions so as to insure meaningful comparative test results for diagnostic evaluation and analysis.

In brief the apparatus herein disclosed employs an upright support frame having force measuring means mounted thereon, first force transmitting means having patient engageable means for transmitting muscle applied forces along a first axis; second transmitting means having additional patient engageable means for transmitting different muscle applied force along a second axis which lies transverse to said first axis and means for transferring forces between the two axes whereby all such muscle applied forces may be transmitted to and measured by the single force sensor measuring means. Means are provided for positioning the patient in a measured location with respect to the apparatus so that comparative test results for a series of time separated evaluations are readily obtainable.

A principal object of this invention is to provide an improved device for measuring selected muscle function of the human anatomy.

Another important object of this invention is to provide muscle measuring apparatus, as set out in the proceeding object, which is distinguished by its simplicity of structure and function and in which patient location relative to the apparatus is measured and defined and is repeatable for successive test sessions.

Still another important object of this invention is to provide apparatus for measuring the strength of selected muscles of the human anatomy in which all patient generated muscle forces are transmitted to a single measuring means along two transversely related force axes.

Having described this invention, the above and further objects, features and advantages thereof will be recognized by those skilled in the art from the following detailed description of a preferred embodiment thereof, illustrated in the accompanying drawings and representing the best mode presently contemplated for enabling those skilled in the art to practice this invention.

IN THE DRAWINGS

DESCRIPTION OF PREFERRED EMBODIMENT

Figure 1:
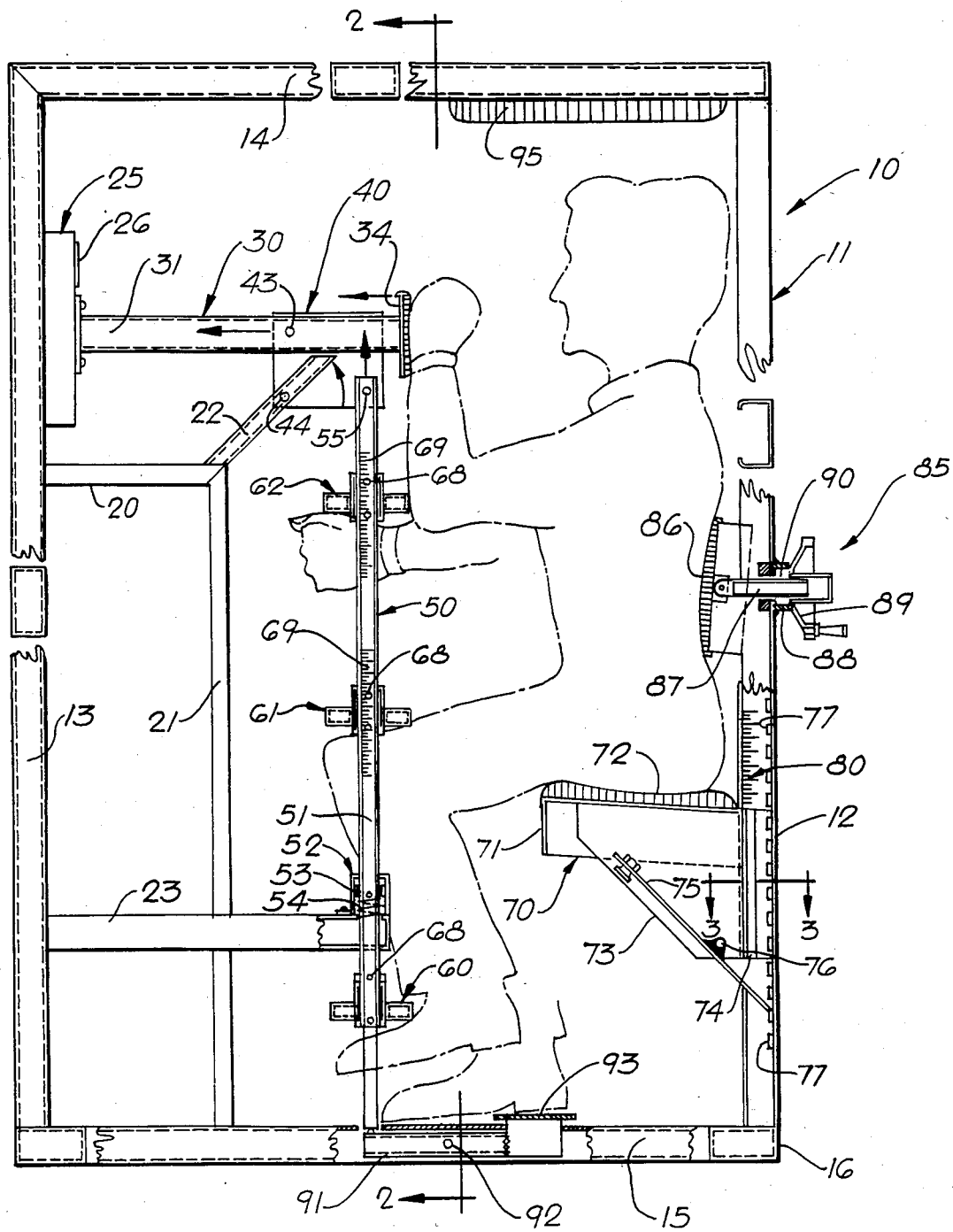
FIG. 1 is a front elevation of muscle measuring apparatus according to this invention, with portions broken away in section.
Figure 2:
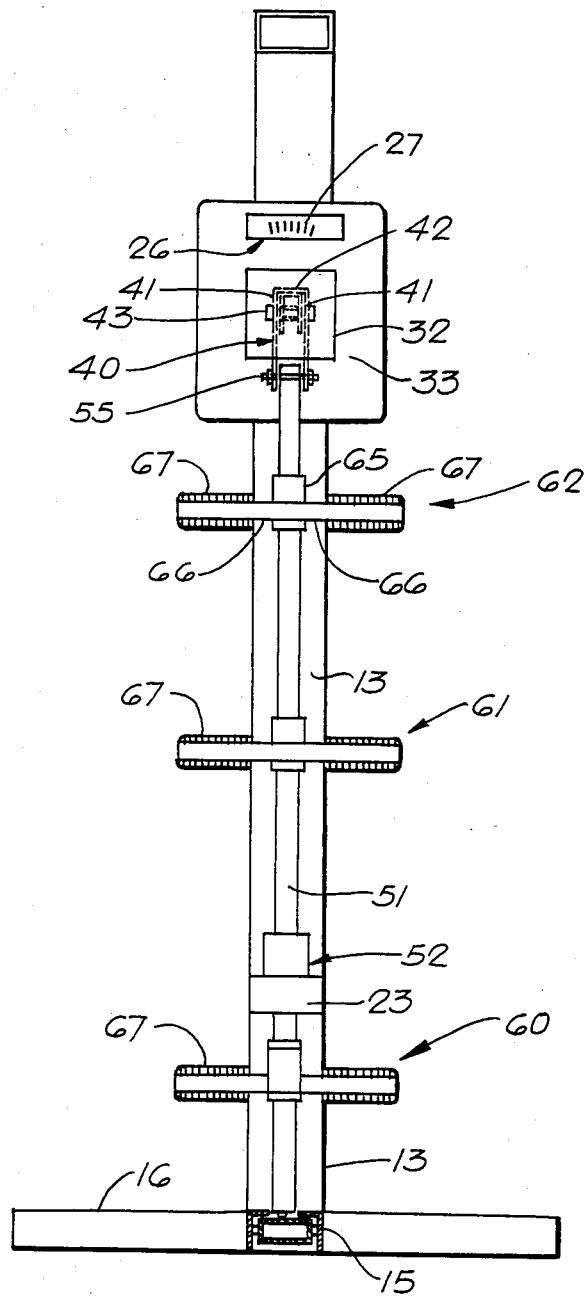
FIG. 2 is a sectional view taken substantially along line 2—2 of FIG. 1 and looking in the direction of the arrows thereon.

With reference to FIGS. 1 and 2, a muscle measuring and evaluating apparatus designated generally at 10, is illustrative of the teachings of this invention. As shown, apparatus 10 comprises a rigid rectangular frame 11 formed by parallel spaced uprights 12, 13 cross connected at their upper and lower ends by horizontal top and base frame members 14 and 15, respectively. The frame numbers 13–15 preferably are formed as metal channels having a closed rectangular cross-section while the one upright 12 is preferably of C-channel cross section, open along one side for purposes which will appear presently. Stabilizing ground engaging legs 16,16 extend transversely across the ends of base frame member 15 and the bottom ends of the upright frame members 12 and 13. The members 12–16 are suitably welded or fixedly joined at their areas of intersection to provide a rigid, vertically upright ground engaging frame structure measuring roughly 5 feet wide and 6 feet high. The use of the tubular channel frame members reduces weight considerably while maintaining desired strength and rigidity so that the frame is readily portable.

Projecting from upright frame member 13 and located intermediate the latter and the other upright frame member 12, is a sub-frame assembly comprising a horizontal tubular member 20 having one end fixed at right angles to vertical tubular frame member 13, and joined at its opposite end to a vertical sub frame member 21. A secondary frame arm 22 extends angularly upwardly from the junction of members 20 and 21 at substantially 45° to the horizontal. Frame member 21 extends through and is welded to a box frame member 23, projecting from upright member 13 parallel to the horizontal sub-frame member 20 and base frame member 15. The lower end of the member 21 is fixed, as by welding, to the base frame member 15.

This sub-frame structure supports a pair of force transmitting means for transferring muscle applied forces to a single stationary measuring means 25 fixed to the upright frame member 13. Such measuring means may comprise any of a number of known dynametric units or force sensor means having suitable scale or other indicator means for measuring recording and visually indicating the applied force. In the particular embodiment illustrated herein, a spring loaded platform scale having dial indicator 26 and read-out scale 27 is utilized as a simplified means for accomplishing the force sensing and measuring function.

In order to transmit muscle applied forces to the measuring means 25, a first force transmitting means 30, comprising an elongated tube 31 of rectangular cross section is employed; such being fastened at one end by flange means 32 to the platform 33 of the illustrated measuring means. Tube 31 is fitted with a pad means 34 at its opposite end for engagement by the hands and arms of the patient, as shown in FIG. 1.

In order to guide and support the tube 31 for limited horizontal movement, the same is coupled to sub-frame arm 22 by means of an intervening transfer linkage means 40 comprising, in the illustrated instance, a unitary metal member of U-shaped cross-section (see FIG. 2) having parallel rectangular side walls 41,41 cross connected along their upper edges by an integral, right angularaly related top wall 42. A first pivot means or bolt 43 moveable within suitable bearings extends laterally through walls 41,41 and the intervening tubular member 31 to pivotally interconnect member 31, at a point intermediate its ends, to transfer linkage means 40. A second pivot means or bolt 44, spaced from pivot means 43 likewise passes laterally through and between walls 41,41 and the intervening frame arm 22 to pivotally attach means 40 to arm 22. Thus translation of tube 31, effects pivotal movement of the transfer linkage means 40 about the two pivot centers 43 and 44, which action serves to support and guide the tube 31 for substantially horizontal movement. A limit to such movement of member 31 is brought about by engagement of the outer end of the angularly extending frame arm 22 with the underside of the tubular member 31. However, sufficient horizontal translation of member 31 is available to actuate the measuring means 25.

A second force transmitting means 50 is also provided to transmit vertically applied muscle generated forces. Means 50 comprises a cylindrical tubular member 51 which passes through a guide bushing assembly 52 located near the outer end of frame member 23. An annular collar 53 is fixed to the member 51 within the assembly 52 to over engage the upper end of compression spring means 54 which operates to resiliently bias the tubular member 51 upwardly and thereby maintain the same in a predetermined vertical position absent vertically applied force supplied by the test subject or patient.

The upper end of member 51 is pivotally pinned by pivot means 55 to one corner of the transfer linkage means 40 which functions as a bell crank. By this means vertical movements of the tubular member 51 cause pivotal activity of transfer linkage means 40 about pivot means 44, producing reactive horizontal translation of the first force transmitting means 40 which is applied thereby to measuring means 25.

Activation of the vertically moveable transmitting means 50 is brought about by the selected application of upwardly directed, patient generated muscular forces through the use of plural patient engageable pad means 60, 61 and 62 mounted on member 51.

Pad means 60 is located near the lower end of the tubular member 51. This pad is primarily engageable by the test subject's feet and toes.

Pad means 61 is located intermediate the ends of member 51 for engagement by the patients knee and thigh.

Pad means 62 is located near the upper end of member 51 for engagement by the patient's wrist and forearm.

It will be recognized that the above discussed spring means 54 acts to render transmitting means 50 effectively weightless with respect to transfer means 40, thereby maintaining the latter in a neutral non-operating position so that it accurately reflects upwardly directed muscle forces applied to the tubular member 51 and the pad means 60-62.

As shown best in FIG. 2, the several pad means 60-62 are alike, each comprising a central mounting collar 65 having tubular arms 66,66 extending coaxially outwardly of opposite side of the collar and fitted with padding covers 67. Collar 65 is fitted coaxially over tubular member 51 and may be fixed thereto or preferably adjustably locked in selected positions thereon by tube engageable lock means 68. If when so adjustably mounted the vertical position of pad means 61 and 62 in particular may be changed, and measured on scale means 69 such measurements are recorded for each patient so that the adjusted pad positions may be repeated for subsequent tests. Normally the toe engageable pad means 60 is not adjusted, but remains stationary at the lower end of tubular member 51.

Figure 3:
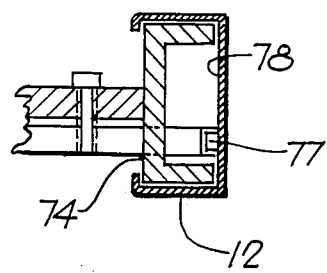
FIG. 3 is an enlarged cross sectional view taken substantially along line 3—3 of FIG. 1 and looking in the direction of the arrows thereon.

In addition to the force transmitting system above-described, the device 10 herein illustrated also includes seat means 70 to permit the patient to be seated during testing. In particular, seat means 70 includes a seat platform 71 having covering pad means 72. A single support gusset 73 extends beneath the seat platform to join a U-shaped support 74 slidingly mounted within the interior of the C-channel frame member 12 (see FIG. 3). Adjustable positioning of the seat is provided by means of a pivotal latch bar 75 welded to a single pivot 76 extending transversely through plate 73 as illustrated in FIGS. 1 and 3. The lower end of the latch bar is adapted to engage a series of vertically spaced blocks 77 welded to the inside of the back wall 78 of the C-channel 12. Cooperating spring means (not shown) or gravity operate to bias the latch bar into engagement with the blocks 77. Thus a releasable ratchet system is provided to locate the seat at desired levels above the floor for purposes of accomodating patients of different size. Appropriate scale means 80 are provided on frame member 12 to indicate the seat position for each patient so that repetition of the patient's seat position may be recorded and repeated for subsequent tests.

An adjustable back rest 85 is also provided on the upright frame member 12 to engage the small of the patient's back while in a sitting position as shown in FIG. 1. The back rest comprises a padded support member 86, pivotally mounted to one outer end of a threaded adjustment post 87. Such post passes through collar 88 fixed to wall 78 of the frame member 12. An adjustment wheel 89 has an extended hub portion 90 mounted to rotate with collar 88. The threaded shank of post 87 is engaged by internal threads of the hub portion 90 to move post 87 coaxially thereof in response to rotative manipulation of wheel 89. Thus the support member 86 may be advanced or retracted to fit the small of the patient's back as desired.

It will be noted that the tubular member 51 extends beyond pad means 60 and passes through the upper wall of frame member 15 where it engages one end of a lever 91 supported centrally of its ends on a horizontal pivot axel 92. The opposite end of lever 91 is equipped with a foot engageable pedal 93 located over frame member 15 as shown in FIG. 1. Depressing pedal 93 activates member 51 upwardly.

This arrangement is useful in measuring the muscle strength of an injured leg; pedal 93 being used in conjunction with a platform scale (not shown) placed on the floor next to frame member 15. The patient steps on the scale to measure his weight. He next steps on pedal 93 with the foot of his injured leg. This procedure permits measuring the downward muscle force enertable by the injured leg by subtracting from the force indicated on scale 27 of the force measuring means 25, the patients' weight. Subsequent such measurements are compared to show progress of the injured leg's muscle strength.

In order to avoid possible injury to the patient's head, suitable padding 95 is provided on the underside of the overhead frame member 14 as shown in FIG. 1.

If desired, the device 10 may also be constructed for stand-up positioning of the patient, in which event the seat and back rest of the illustrated sit-down model are eliminated and the upright frame members 11 and 13 are extended or constructed for vertical adjustment to accommodate different height patients.

USE AND OPERATION

Having described the structural features of a measuring device according to this invention its operation and functioning now will be described briefly.

Basically, the described device is intended to analyze the functioning of selected muscles by duplex testing of corresponding muscles on both the left and right sides of the body. This approach checks body symmetry from which a skilled physician may diagnose the condition of particular muscles and associated nerves. Lack of muscular symmetry is indicative of slipped discs of the spinal column, squeezed or pinches nerves or simlar column disorders and points to possible damage to the brain and/or related internal organs.

With the above in mind the device 10 is principally designed to test the functioning of six muscles, namely the biceps and triceps of the left and right arms and the psoas for the left and right legs and thighs. The results of such tests provide a most satisfactory analysis of the patient's body symmetry and columnor functions. In the illustrated case, when the patient pushes horizontally on pad 34 and vertically upward on member 62, the left and right biceps and triceps of both arms are tested. Upward pushing by the patient's thighs or knees against the member 61, first one side (right) and then on the opposite side (left) test the right and left psoas. Similarly, psoas testing takes place by engaging member 60 and pushing upwardly, by first the right foot and then the left, or vice versa. By recording the readings indicated on the measuring means 25 resulting from each test the examining physician obtains data which may be charted and is available for review and comparison with successive or subsequent test results to show improvement or deterioration of the patient's condition. Thus, the doctor's feel and memory of the patient's muscle condition is eliminated by use of this invention.

While the particular described embodiment shown and described is intended to test six muscles as related, it is fully contemplated that additional muscles may be tested as well, either by using the several pad means 34, 60–62 shown or by adding additional pad means in different locations. For example, a patient's neck muscles may be tested by engaging means 34 with the forehead or the back or sides of the head to actuate transmitting means 30. Similarly toe or ankle engagement of means 62 may be used to test muscles related to specific toes or those related to various ankle movements, etc.

In view of the foregoing it is believed that those skilled in the art will readily recognize the improved advancement presented by this invention and will understand that while the same herein has been described in association with a preferred embodiment of its teachings, illustrated in the accompanying drawings, such is susceptible to variation, modification and substitution of equivalents without departing from the scope of the invention which is intended to be unlimited by the foregoing except as may appear in the following appended claims.

We claim:

1. Apparatus for evaluating selected muscles of the human anatomy comprising: ground engaging frame means having a pair of parallel vertically upright frame members, force sensor means including measuring means stationarily supported on said frame means, first force transmitting means mounted for movement along a first axis and arranged to transmit muscle applied force to said sensor means, second force transmitting means arranged to transmit muscle applied force along a second axis transverse to said first axis, force transfer means connected to said first and second transmitting means and arranged to cconvert movements of said second transmitting means into movement of said first transmitting means, and patient engageable means associated with each of said transmitting means for engagement by selected areas of the human body whereby the force producing capability of specific muscles associated with said areas is applied to said transmitting and sensor means.

2. The apparatus of claim 1, wherein said first and second transmitting means comprise linearly moveable elongated members operable to move horizontally and vertically, respectively.

3. The apparatus of claim 2, wherein said transmitting means are intersectingly aligned and said transfer means is located at the zone of intersection thereof.

4. The apparatus of claim 1, and means supporting the weight of said second transmitting means and said patient engageable means thereon whereby to maintain said transfer means in a predetermined, neutral, non-operating position so that movement of said second transmitting means is accurately reflective of muscle forces applied thereto.

5. The apparatus of claim 1, wherein said patient engageable means on said second transmitting means includes one or more of such patient engageable means comprising means for adjustably positioning the same to conform to the patient's physique.

6. The apparatus of claim 5, and means to indicate the adjusted position of said one or more patient engageable means.

7. The apparatus of claim 1, wherein said sensor means is mounted at an elevated position, and said first transmitting means comprises a substantially linearly moveable member engageable with siad sensor means to actuate the same.

8. The apparatus of claim 1, and adjustable seat means mounted on one of said upright frame members, and means for determining the adjusted position of said seat means thereon.

9. The apparatus of claim 1, wherein said transfer means comprises, a stationary support adjacent said transfer means, first and second spacially separated pivot means joining said transfer means to said first and second transmitting means, respectively, and third pivot means joining said transfer means to said support.

10. The apparatus of claim 1, wherein said transfer means is pivotally connected to said first and second transmitting means at separate horizontal pivot axes, and said transfer means is pivotally supported for movement about a horizontal axis remote from the pivotal connections thereof with said transmitting means; said transfer means being operable to convert vertical movement of said second transmitting means into horizontal movement of said first transmitting means.

* * * * *